(12) United States Patent
Jackson et al.

(10) Patent No.: US 6,371,934 B1
(45) Date of Patent: *Apr. 16, 2002

(54) IRRIGATION SYSTEM AND TIP WITH DEBRIDER

(75) Inventors: Robert W. Jackson, Dallas, TX (US); Karen E. Kullas, Taunton, MA (US); Augustus Felix, Cranston, RI (US); Richard P. Rego, Jr., Mansfield, MA (US)

(73) Assignee: C. R. Bard, Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/907,348

(22) Filed: Aug. 6, 1997

(51) Int. Cl.$^7$ .......................... A61M 1/00; A61B 17/22
(52) U.S. Cl. ......................... 604/35; 606/159; 604/267
(58) Field of Search .............................. 604/22, 27, 35, 604/39, 43, 118, 117, 160, 170, 173, 266, 267; 606/107, 169–171, 159; 601/160, 162, 165

(56) References Cited

U.S. PATENT DOCUMENTS

| | | |
|---|---|---|
| 4,027,658 A | 6/1977 | Marshall |
| 4,076,032 A | 2/1978 | Misercola |
| 4,517,701 A * | 5/1985 | Stanford, Jr. ................ 15/106 |
| 4,604,089 A | 8/1986 | Santangelo et al. |

(List continued on next page.)

FOREIGN PATENT DOCUMENTS

| | | |
|---|---|---|
| GB | 2320683 | 7/1998 |
| WO | WO9724993 | 7/1997 |

OTHER PUBLICATIONS

Srague, III, "Arhtroscopic Debridement for Degenerative Knee Joint Disease", Clinical Orthopaedics and Related Research, No. 160, Oct. 1981, pp. 118–123.

Baumgaertner, et al., "Arthroscopic Debridement of the Arthritic Knee", Clinical Orthopaedics and Related Research, No. 253, Apr. 1990, pp. 197–202.

Aichroth, et al., A Prospective Review of Arthroscopic Debridement for Degenerative Joint Disease of the Knee , International Orthopaedics, vol. 15, 1991, pp. 351–355.

Skyhar, et al., "Arthroscopic Treatment of Septic Knees in Children", Journal of Pediatric Orthopaedics, vol. 7, No. 6, 1987, pp. 647–651.

Gross, et al., "Arthroscopic Treatment of Dengeerative Joint Disease of the Knee", Orthopedics, vol. 14, No. 12, 1991, pp. 1317–1321.

Bert, "Role of Abrasion Arthroplasty and Debridement in the Management of Osteoarthritis of the Knee", Osteoarthritis, vol. 19, No. 3, Aug. 1993, pp. 725–739.

Davol/Bard Simpulse® Solco Pulsed Lavage System brochure, #OP 0067620–R, 6/95.

Davol/Bard New Simpulse® Plus Pulsed Lavage brochure, #OP 0057570, 9/94.

(List continued on next page.)

Primary Examiner—Anhtuan T. Nguyen
(74) Attorney, Agent, or Firm—Kirkpatrick & Lockhart LLP

(57) ABSTRACT

An improved irrigation system for removing arthritis causing fragments from a joint in the body includes a handpiece and a tip that is connectible to the handpiece. The tip includes a shaft that forms an irrigation lumen, and a debrider disposed along at least a part of the shaft. The debrider defines a substantially planar debriding surface for debriding the interior surfaces of the joint. The debrider may include a plurality of bristles extending from the shaft to the debriding surface.

14 Claims, 7 Drawing Sheets

FOREIGN PATENT DOCUMENTS

| | | | |
|---|---|---|---|
| 4,625,725 | A | 12/1986 | Davison et al. |
| 4,655,197 | A | 4/1987 | Atkinson |
| 4,692,140 | A | 9/1987 | Olson |
| 4,919,153 | A | 4/1990 | Chin |
| 4,940,457 | A | 7/1990 | Olson |
| 5,197,949 | A | 3/1993 | Angsupanich |
| 5,217,023 | A | 6/1993 | Langdon |
| 5,322,506 | A | 6/1994 | Kullas |
| 5,484,281 | A * | 1/1996 | Renow et al. .......... 601/162 X |

OTHER PUBLICATIONS

Davol/Bard Simpulse® Plus Lavage brochure, #OP3759.

Davol/Bard Arthroscopy Irrigation and Instrument Cannulas, #OP3781.

Stryker Surgilav® Plus Spike & Shoot brochure, #1000–164 REV A 1/94.

Stryker Surgical Excel, #4500 001 121 JJB 12/88.

Zimmer Pulsavac Wound Debridement System brochure, #97–5150–604.

Bierbaum, B.E., "High Pressure, Pulsatile Lavage in Wound Management", A Literature Review, Davol, Inc., 1986.

Jackson, R. W., et al., "Point–Counterpoint—Arthroscopic Debridement Versus Arthroplasty in the Osteoarthritic Knee", *The Journal of Arthroplastay*, vol. 12, No. 4, 1997, pp. 465–470.

Jackson, R.W, "Arthroscopic Surgery and a New Classification System", *The American Journal of Knee Surgery*, Winter 1998, vol. 11, No. 1, pp. 51–54.

* cited by examiner

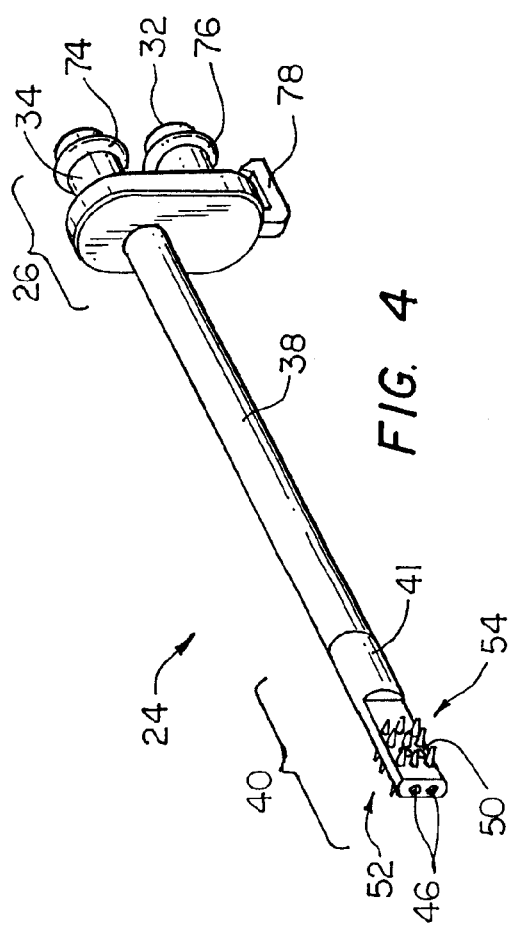
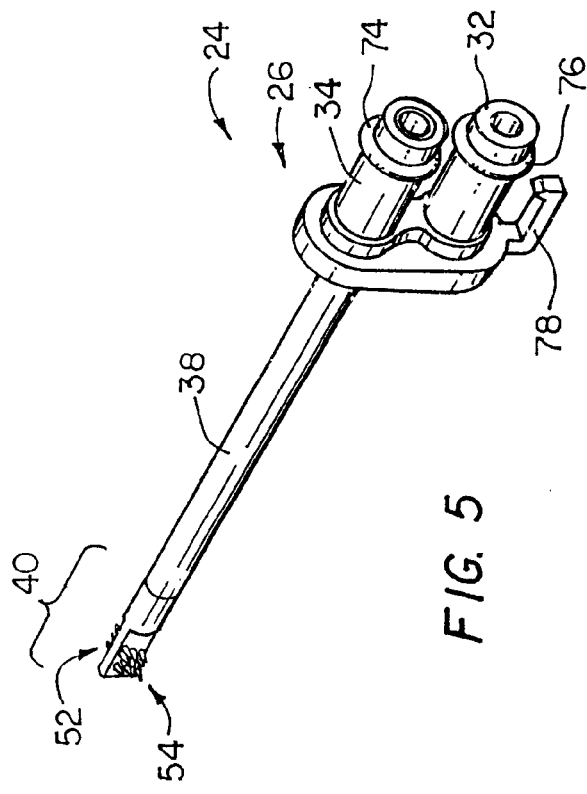

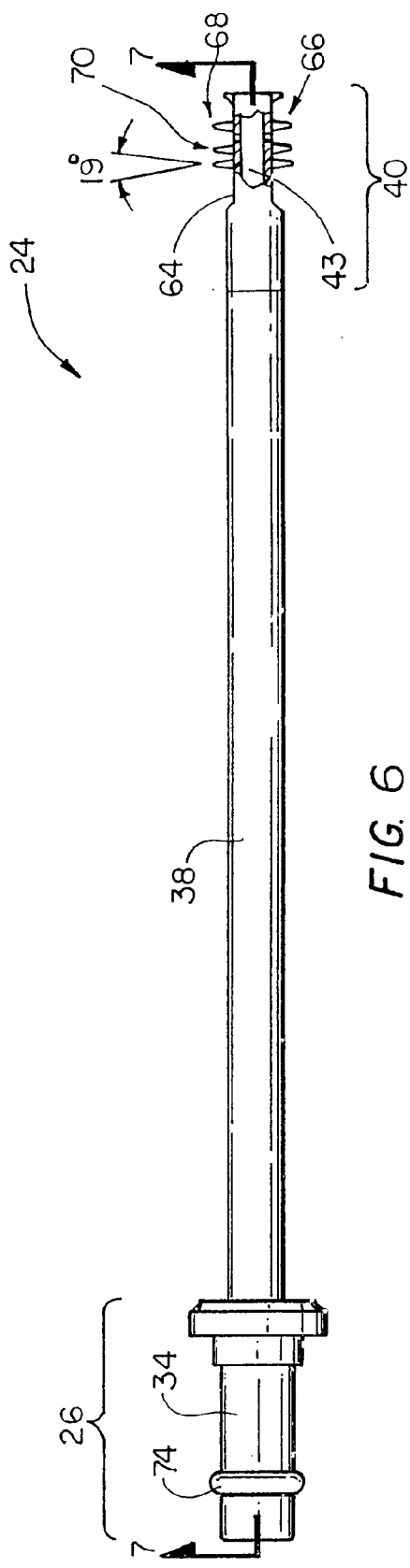
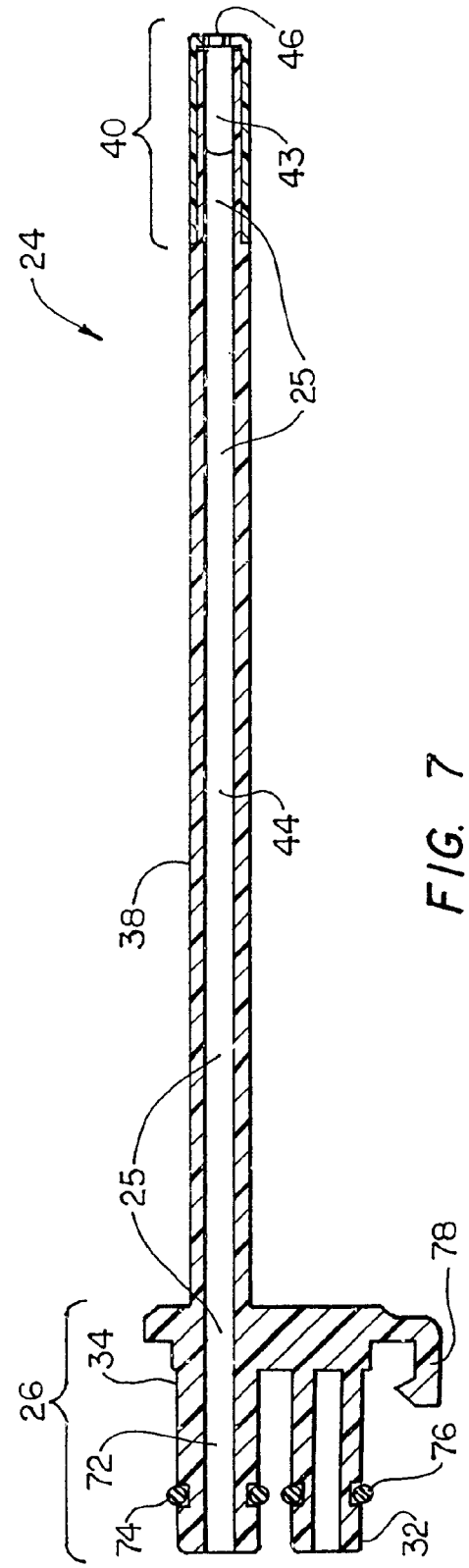
FIG. 6
FIG. 7

IRRIGATION SYSTEM AND TIP WITH DEBRIDER

FIELD OF THE INVENTION

This invention generally relates to irrigating and arthroscopically treating an arthritic joint.

BACKGROUND OF THE INVENTION

Degenerative osteoarthritis ("arthritis"), a painful joint disorder, is caused by fragments of bone, articular cartilage, and calcium pyrophosphate crystals that form on and/or adhere to the interior surfaces of an affected joint in the body. The fragments irritate and inflame the joint, causing discomfort.

There are a number of treatments for arthritis. One such treatment uses an anti-inflammatory medicine, such as ibuprofen, to reduce swelling within the joint. Although such treatment may relieve the symptoms of arthritis, it does not treat the cause of the inflammation (i.e., the fragments). Accordingly, arthroscopic surgery often is necessary in more severe cases to physically remove the fragments from within the joint.

One common arthroscopic fragment removal treatment, tidal lavage, employs an irrigation inflow cannula to provide a steady flow of irrigation liquid into the joint, and an irrigation outflow cannula to remove the irrigation liquid from the joint. Steady flow of liquid through the joint is intended to flush some of the fragments from the interior joint surfaces through the outflow irrigation cannula. The procedure, however, does not forcefully remove the fragments, consequently leaving some fragments lodged in the joint. The remaining fragments may continue to irritate and inflame the joint. Accordingly, a fragment removal treatment that more forcefully removes the fragments often is necessary.

One known forceful fragment removal procedure employs a hand-held, motor driven, metal instrument such as, for example, an arthroscopic shaver device. Although such motor driven devices may remove many fragments that are not removable with tidal lavage, they present a risk of trauma and further damage to the interior surfaces of the joint. Another problem with motor driven instruments is that they may be relatively ineffective for removing very small fragments that cannot be readily viewed by an arthroscope.

It therefore would be desirable to provide an arthroscopic irrigation device and technique to effectively and safely remove arthritis causing fragments from within a joint.

SUMMARY OF THE INVENTION

The invention includes an irrigation tip, for use with a handpiece, that has both mechanical means and liquid means for removing fragments from interior surfaces of a joint. The tip includes an elongate shaft having an irrigation lumen and a debrider disposed along at least a segment of the outer surface of the shaft. The debrider defines a substantially planar debriding surface, thereby providing a relatively uniform and large surface area for removing fragments from interior surfaces of the joint.

It is among the general objects of the invention to provide an apparatus that more efficiently removes arthritis causing fragments from within a joint in the body.

It is another object of the invention to provide an apparatus that removes arthritis causing fragments from a body, joint more forcefully, and more completely, than the tidal lavage technique.

It is also object of the invention to provide an apparatus that removes arthritis causing fragments from a body joint less forcefully, but more completely, than the techniques employing motor driven devices.

It is another object of the invention to provide an apparatus having both liquid means and mechanical means for removing arthritis causing fragments from within a body joint.

BRIEF DESCRIPTION OF THE DRAWINGS

The foregoing and other objects and advantages of the invention will be appreciated more fully from the following further description thereof, with reference to the accompanying drawings wherein:

FIG. 4 is an oblique view of the irrigation tip shown in FIG. 1;

FIG. 5 is a rear view of the irrigation tip shown in FIG. 1;

FIG. 6 is a top view, cut away in part, of the assembled tip shown in FIG. 6;

FIG. 7 is a side cross-sectional view of the tip shown in FIG. 6 along lines 7—7 of FIG. 6;

DESCRIPTION OF THE ILLUSTRATIVE EMBODIMENT

Figure 1:
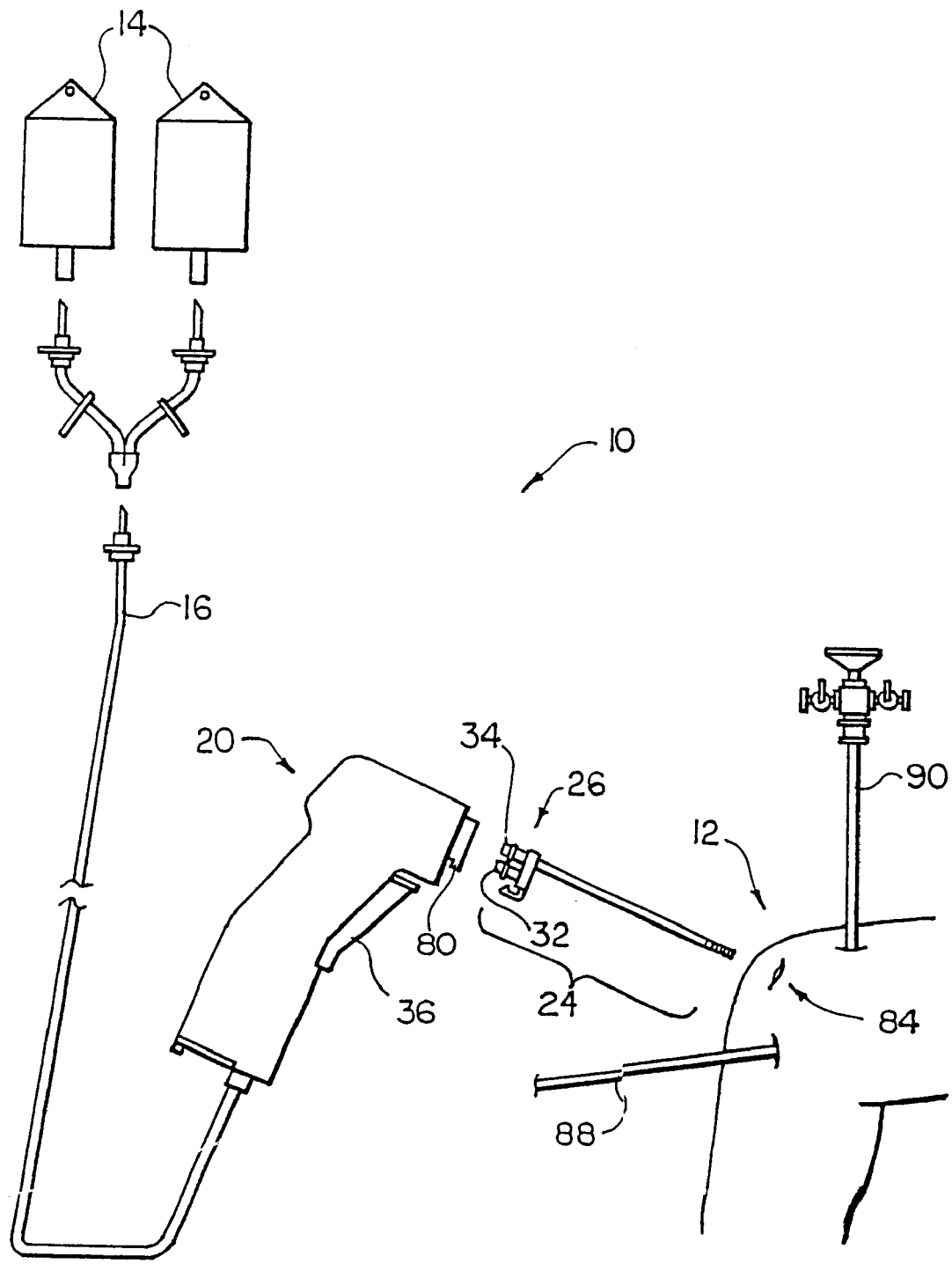
FIG. 1 is an illustration of an irrigation system in accordance with the invention.

The term "debride" shall be used to mean removal of fragments from interior surfaces of a joint. FIG. 1 shows a preferred embodiment of a system 10 for debriding a joint 12 in the body, such as a knee. The system 10 includes a reservoir 14 containing a sterile irrigation liquid, typically saline. The reservoir 14 is connected by a flexible tubing 16 that extends to a handpiece 20. The handpiece 20 controls the delivery of irrigation liquid from the reservoir 14 to the joint 12, and is detachably connectible to an elongate tip 24 that is adapted to be inserted into the joint 12. The tip 24 has an irrigation lumen 25 (FIG. 7) that extends the full length of the tip 24 and is open at its distal end to emit the irrigation liquid into joint 12.

Although the handpiece 20 may be any desired configuration, the invention is illustrated in connection with a preferred handpiece 20, such as that disclosed in co-pending U.S. patent application Ser. No. 08/389,155, filed Feb. 5, 1995 (Pasch et al.) now U.S. Pat. No. 5,746,721, the entire disclosure of which is incorporated herein by reference. As disclosed in further detail in that application, the handpiece 20 includes a self-contained pulsatile pump mechanism, batteries for driving the pump mechanism, and a control system for controlling the flow of liquid through the system. The handpiece 20 may be somewhat pistol shaped and has a fitting 22 at one end that can be detachably coupled to a tip connector 26 on the proximal end of the tip 24. The fitting 22 includes suction and irrigation ports (not shown) that mate with corresponding suction and irrigation plugs 32 and 34 on the tip connector 26. Since the preferred embodiment of the tip 24 does not include a suction lumen, the plugs 32 and 34 are constructed to communicate only irrigation liquid from the handpiece 20 to the tip lumen. No suction from the handpiece fitting 22 is communicated through the tip 24. Reference is made to the application Ser. No. 08/389,155 for further details of the suction and irrigation ports on the fitting.

The handpiece 20 also includes a trigger 36 that, when squeezed, closes electrical contacts within the handpiece 20 to initiate operation of the pumping mechanism (not shown) within the handpiece 20. This causes a pulsatile flow of irrigation liquid to be delivered to the body joint 12 through the tip 24.

FIGS. 2–8 show several views of a preferred embodiment of the tip 24, which includes the connector 26 for connecting the tip 24 to the handpiece 20, an elongate shaft 38 extending approximately five inches from the connector 26, and a flexible debrider 40 (manufactured from a more flexible material than the shaft 38) secured to the distal end of the shaft 38. The debrider 40 has substantially planar debriding surfaces 66 and 68 (FIG. 3) to provide a relatively uniform and large surface area for removing fragments from interior joint surfaces.

Figure 2:
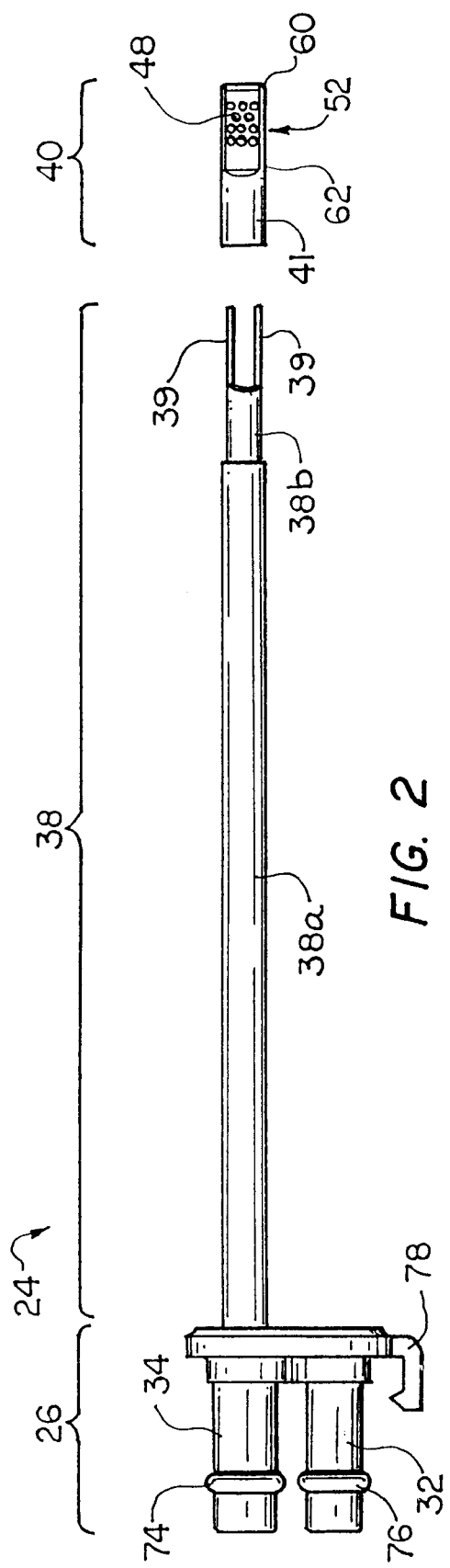
FIG. 2 is a side exploded view of the tip shown in FIG. 1.
Figure 3:
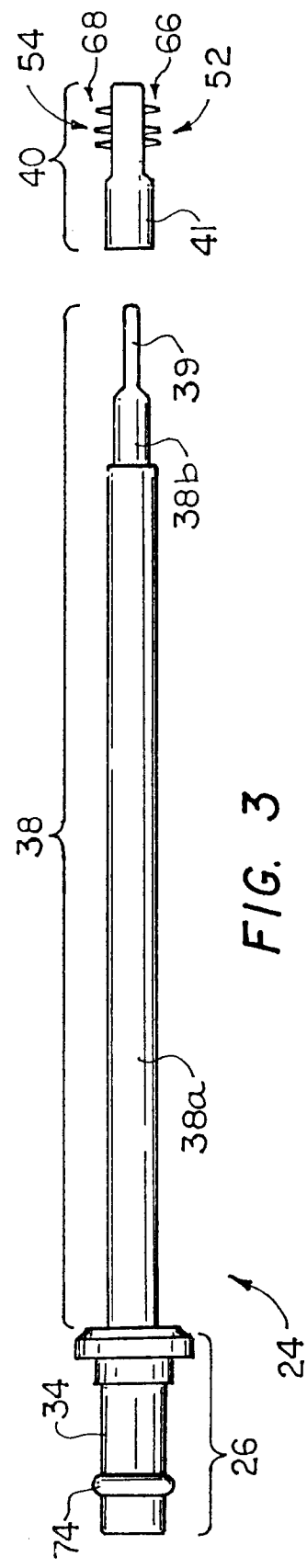
FIG. 3 is a top exploded view of the tip shown in FIG. 1.
Figure 8:
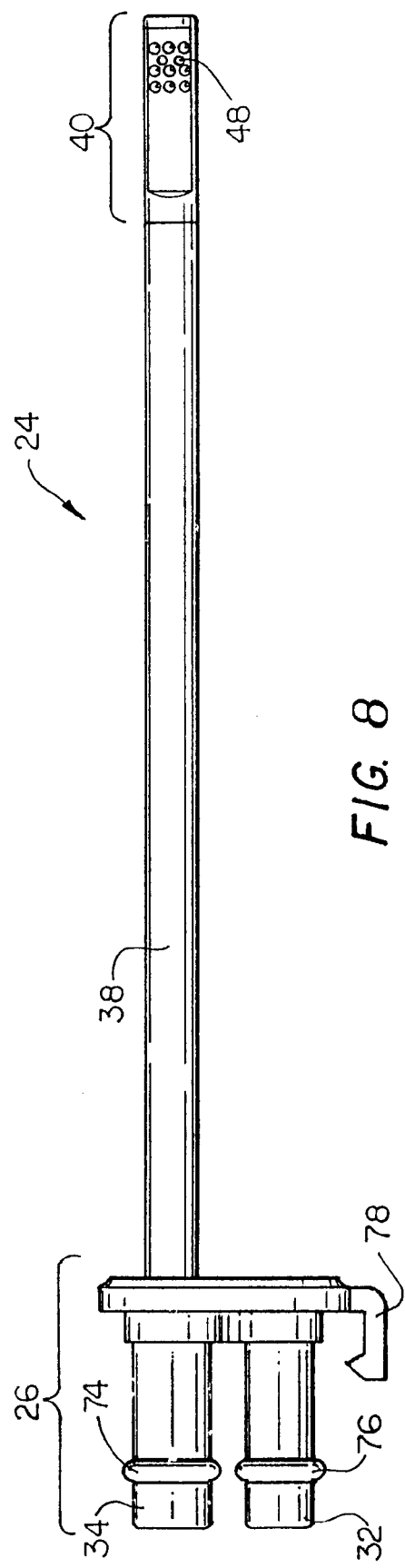
FIG. 8 is a side view of the assembled tip shown in FIG. 1.

As shown in FIGS. 2 and 3, the shaft 38 preferably includes a proximal portion 38a, a distal portion 38b having a smaller outer diameter than the proximal portion 38a, and two distally extending fingers 39. The debrider 40 includes a proximal connecting portion 41 having an inner diameter that is approximately equal to the outer diameter of the shaft distal portion 38b, and an interior chamber 43 (FIGS. 6 and 7) having a maximum cross-sectional dimension that is substantially equal to the inner diameter of a shaft lumen 44 (discussed below) formed through the shaft 38. When assembled (FIGS. 4–8), the fingers 39 are positioned within the interior chamber 43 to partially support the flexible debrider 40, and the proximal connecting portion 41 of the debrider 40 is received over the shaft distal portion 38b. The debrider 40 and shaft 38 may be bonded together by means of an adhesive.

The outer diameter of the shaft proximal portion 38a and debrider connection portion 41 preferably is about 0.20 inches to facilitate insertion into the joint 12. It is expected that a maximum outer dimension of about 0.35 inches for these portions 38a and 41 should produce satisfactory results. The shaft 38 includes the shaft lumen 44, having a uniform inner diameter, that directs irrigation liquid to a plurality of irrigation holes 46, 48, and 50 in the debrider 40. Specifically, the debrider 40 includes a pair of longitudinal irrigation outlet holes 46 (FIG. 4), a first pair of radial irrigation holes 48 (FIG. 2), and a second pair of radial irrigation holes 50 (FIG. 4). Irrigation liquid is delivered into the joint from the tip lumen 25 through the irrigation outlet holes 46, 48, and 50.

In the preferred embodiment, the debrider 40 includes first and second sets of flexible bristles 52 and 54, extending from opposite surfaces of the debrider 40, that each respectively terminate at the substantially planar debriding surfaces 66 and 68. The opposite surfaces may be on any circumferential part of the debrider 40 such as, for example, the sides 56 of the debrider 40, or the top and bottom 58 of the debrider 40. Since both sets of flexible bristles are constructed and arranged identically, only the first set of bristles 52 will be discussed in detail. It should be understood, however, that the details mentioned relative to the first set of bristles applies identically to the second set of bristles 54.

The first set of bristles 52 is positioned on the debrider between a distal shoulder 60 and a proximal shoulder 62. The shoulders 60 and 62 preferably have a maximum outer dimension that is substantially equal to the maximum outer dimension of the shaft 38. Accordingly, the shoulders 60 and 62 define a recessed surface 64 from which the bristles extend. In the preferred embodiment, the bristles 52 extend approximately to the outer diameter of the shaft 38 and shoulders 60 and 62.

Although not necessary, the recessed surface 64 from which the first set of bristles extends preferably is substantially planar. The bristles preferably extend between about 0.024 to 0.036 inches from the recessed surface 64. The first set of bristles 52 extends from such surface 64 to the debriding surface 66. The first set of bristles 52, which are integral with and manufactured from the same material as the debrider 40, preferably includes three rows of bristles, each row having three bristles. The first two rows of bristles from the proximal end of the debrider 40 may be spaced approximately 0.05 inches apart. The third row of bristles (nearest the distal end of the debrider 40), however, is spaced approximately 0.08 inches from the second row to provide space for the first pair of radial irrigation holes 48. Similarly, the bristles in the individual rows of bristles are spaced approximately 0.05 inches apart. The bristles preferably converge upwardly at an angle of approximately nineteen degrees (FIG. 6) to terminate in a somewhat rounded bristle tip 70. Like the first set of bristles 52, the second set of bristles 54 includes the planar debriding surface 68 and, as previously noted, is formed identically. In an alternative embodiment, the debrider 40 may include the first set of bristles 52 only.

Each of the irrigation holes 46, 48, and 50 preferably is configured to emit irrigation liquid in a liquid stream having a substantially uniform diameter. In the preferred embodiment, the irrigation liquid is emitted at a maximum stagnation pressure of approximately thirty pounds per square inch with a force of about thirty pounds per square inch. It also is preferred that the irrigation liquid be emitted at a pulsatile frequency of approximately 1,500 cycles per minute with a flow rate of approximately 1,300 milliliters per minute. To that end, the irrigation holes 46, 48, and 50 preferably are approximately cylindrically shaped and may have a uniform diameter of the order of 0.025 inches. In an alternative embodiment, the irrigation holes 46, 48, and 50 may be tapered to emit irrigation liquid in a conical spray pattern.

The connector 26 includes the suction and irrigation plugs 32 and 34 that are insertable into the suction and irrigation ports on the handpiece fitting 22. This frictionally secures the tip 24 to the handpiece 20. The irrigation plug 34 includes a longitudinal plug lumen 72 (FIG. 7) extending from the shaft irrigation lumen 44 to the proximal end of the tip 24. The plug lumen 72, shaft lumen 44, and interior chamber 43 of the debrider 40 together form the tip lumen 25. When connected to the handpiece 20, the irrigation plug 34 fluidly communicates the tip lumen 25 with the handpiece 20. A first rubber O-ring 74 may encircle a part of the irrigation plug 34 to both fluidly seal and frictionally secure the tip connection to the handpiece 20. Unlike the irrigation plug 34, the suction plug 32 does not include means for fluidly communicating with the tip lumen 25 and thus, is provided merely to support the tip 24 in the fitting 22. A second rubber O-ring 76 may encircle a part of the suction plug 32 to provide a more secure frictional fit to the handpiece 20. The connector 26 also includes a proximally extending clip 78 to detachably connect to a depending lip 80 on the handpiece fitting 22.

Figure 9:
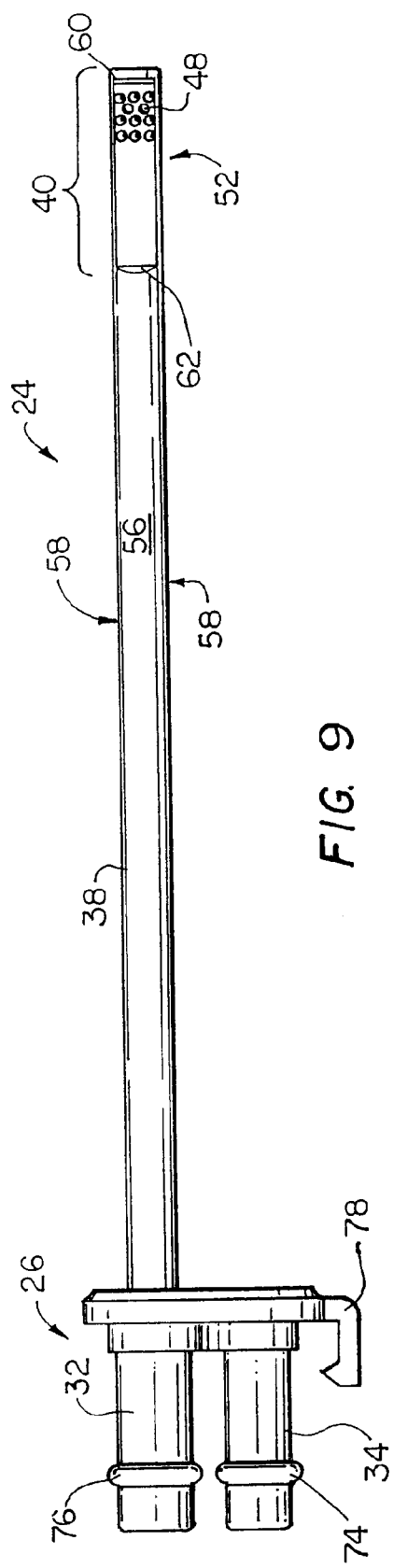
FIG. 9 is an alternative embodiment of the tip shown in FIG. 1.
Figure 10:
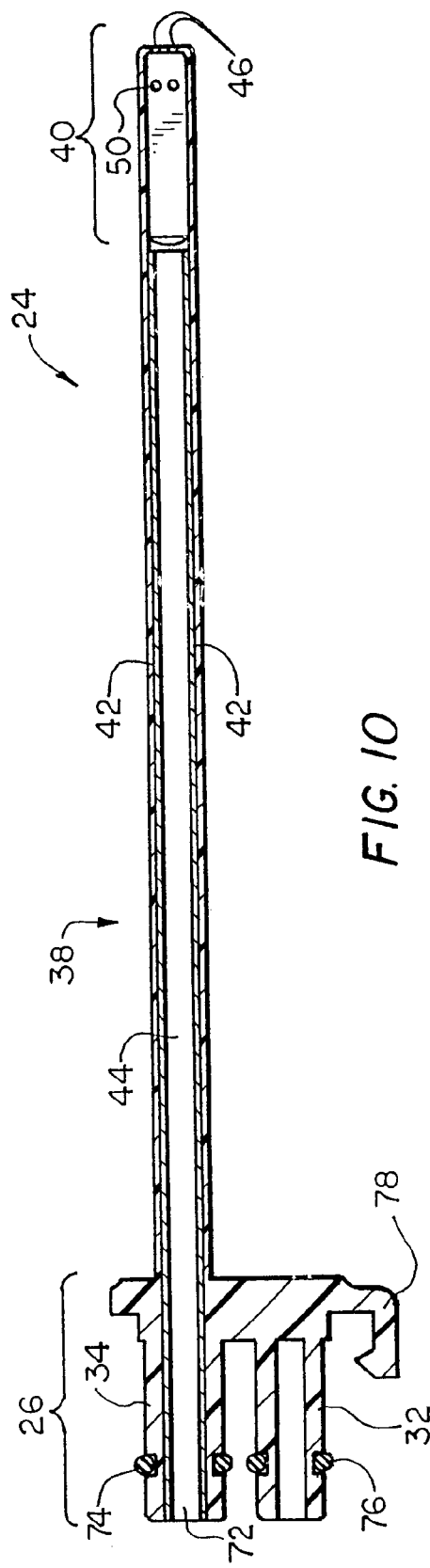
FIG. 10 is a side cross-sectional view of the tip shown in FIG. 9.

In an alternative embodiment shown in FIGS. 9 and 10, a rigid stainless steel tube 42 may be disposed through the plug lumen 72 and shaft lumen 44 to further stiffen the shaft 38, thus enabling a physician to more forcefully press the distally located debrider against an interior joint surface. The outer diameter of the rigid tube 42 should be approximately equal to that of the shaft lumen 44. This enables the tube 42 to be securely fastened, by means of a press fit, to the wall of the shaft lumen 44. The tube 42 preferably is approximately 5.25 inches long and extends from the proximal end of the irrigation plug lumen 72 to the proximal shoulder 62.

In another alternative embodiment also shown in FIGS. 9 and 10, the shaft 38 and debrider 40 are a single unitary piece manufactured from a polymeric material by conventional injection molding processes. The rigid tube 42 also may be disposed through the shaft lumen 44 in this embodiment to stiffen the tip structure.

Figure 11:
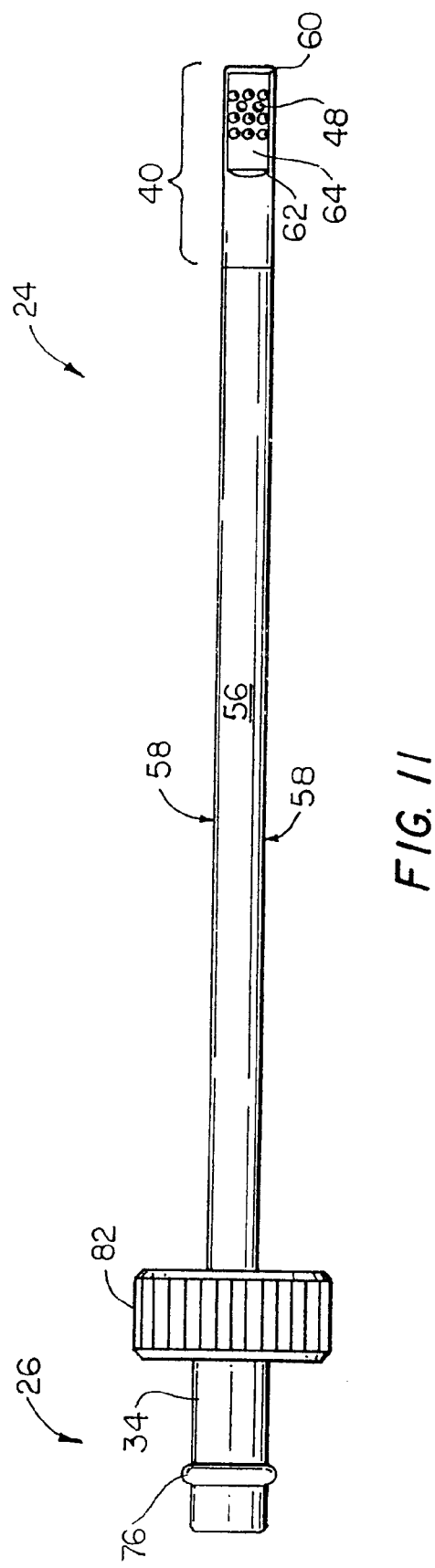
FIG. 11 is another alternative embodiment of the tip shown in FIG. 1.

FIG. 11 shows another alternative embodiment of the tip 24 having a knob 82 for rotating the tip 24 while connected to the handpiece 20. This enables a physician to re-orient the tip 24 in the joint without re-orienting the handpiece 20. To that end, the clip 78 and suction plug 32 are omitted from the connector 26, and the knob 82 encircling the proximal end of the shaft 38 is included. Rotation of the knob 82 causes the tip 24 to rotate in the fitting irrigation port about the longitudinal axis of the irrigation plug 34.

The connector 26 and shaft 38 preferably are a one-piece structure manufactured from a rigid material, such as polycarbonate or acrylic. Conversely, the debrider 40 preferably is manufactured from a flexible polymeric material, such as plasticized polyvinyl chloride (PVC) having a durometer of approximately 85 Shore-A and a modulus of elasticity of approximately 1,500 to 1,600 pounds per square inch.

In use, as shown in FIG. 1. the handpiece 20 is connected to the reservoir 14 by the flexible tubing 16, and the tip 24 is connected to the handpiece 20. The tip 24 then may be inserted into the joint 12 (knee) through a cannula or hole 84 in the knee. The region about the joint 12 is distended by the inflow of liquid through an inlet cannula (which may be a part an arthroscope 90) and is drained through an outlet cannula 88. The arthroscope 90, inserted into the joint 12 through another hole in the knee, also provides a means for viewing the interior of the knee joint 12 during the procedure. The pulsatile irrigation liquid then may be emitted throughout the interior surface of the joint 12 to dislodge fragments. The debriding surfaces 66 and 68 of the debrider 40 also may be brushed against interior surfaces of the knee, with or without the pulsatile irrigation stream, to further debride bone, cartilage, or tissue within the joint 12. The debriding surfaces 66 and 68 should efficiently debride interior surfaces of the joint 12 since they each form a substantially uniform and large debriding surface. Trauma to the interior surfaces of the joint 12 is minimized because the debrider 40 is manufactured from a flexible, relatively soft material as described above. Moreover, the rigidity of the tube 42 prevents the shaft 38 from bending, under expected operating leverage forces, thus enabling the debrider 40 to more forcefully remove fragments from the interior joint surfaces.

Fragments detached from the interior surfaces of the joint 12 by the tip 24 may be flushed from the knee joint 12 by the outflow of the irrigation liquid through the outlet cannula 88. Although not necessary in many cases, the tip 24 then may be removed from the handpiece 20 and a suction tip (not shown) may be attached to the handpiece 20 to further remove detached fragments from the joint 12. The suction tip directs suction from an external suction source to the interior of the joint 12.

From the foregoing, it should be appreciated that the invention provides an improved debridement device for use in removing fragments from within an arthritic joint. The system 10 should debride an arthritic joint more efficiently and with less wound trauma than prior art joint debridement devices. It should be understood, however, that the foregoing description of the invention is intended merely to be illustrative thereof and that other embodiments, modifications, and equivalents may be apparent to those skilled in the art without departing from its spirit.

Having thus described the invention what we desire to claim and secure by Letters Patent is:

1. In an irrigation tip for arthroscopic insertion into a joint, the tip being adapted for use with a handpiece, the tip having an elongate shaft defining an irrigation lumen; and a connector for connecting the shaft to the handpiece; the improvement comprising a debrider disposed along at least part of the shaft, the debrider defining a substantially planar debriding surface and including a plurality of bristles, the tips of which define the debriding surface.

2. The irrigation tip as defined by claim 1 further comprising a radially extending irrigation hole proximally of the distal extremity of the tip.

3. The irrigation tip as defined by claim 1 wherein the debrider further comprises a second substantially planar debriding surface.

4. The irrigation tip as defined by claim 3 wherein the second substantially planar debriding surface comprises a plurality of bristles the tips of which define the second debriding surface.

5. The irrigation tip as defined by claim 1 further comprising a rigid tube within the irrigation lumen.

6. The irrigation tip as defined by claim 1 further comprising a knob mounted to the shaft.

7. The irrigation tip as defined by claim 1 further comprising an irrigation hole extending longitudinally through the distal end of the shaft.

8. An irrigation tip as defined in claim 1 further comprising:
   at least that portion of the irrigation tip that includes the debrider being more flexible than the more proximally disposed portion of the tip.

9. A tip as defined in claim 8 wherein the material from which the debrider is formed has a lower modulus of elasticity than that of the material from which the shaft is formed.

10. A system for arthroscopically debriding a surface within a body joint comprising:
    a handpiece; and
    an irrigation tip as defined in claim 1.

11. The system as defined by claim 10 wherein the handpiece includes a pulsatile pump for emitting irrigation liquid in a pulsatile flow.

12. An irrigation tip for arthroscopic insertion into a body joint, the tip being adapted for use with a handpiece, the tip comprising:
    an elongate shaft defining an irrigation lumen;
    a connector at the proximal end of the shaft for connecting the shaft to the handpiece;
    a debrider assembly attached to the shaft and defining the distal end of the shaft, the debrider assembly comprising a plurality of bristles that define a substantially planar debrider surface.

13. An irrigation tip as defined in claim 12 wherein the tip further comprises;

that portion of the shaft in the region of the debrider having a reduced transverse dimension that defines a recessed surface with respect to the other portions of the shaft; the bristles extending radially outwardly from the recessed surface.

14. An irrigation tip as defined in claim 13 wherein the recessed surface is substantially flat.

* * * * *